US00PP24847P3

(12) United States Plant Patent
Korlipara

(10) Patent No.: US PP24,847 P3
(45) Date of Patent: Sep. 2, 2014

(54) ***COREOPSIS* PLANT NAMED 'DESERT CORAL'**

(50) Latin Name: ***Coreopsis* hybrid**
Varietal Denomination: Desert Coral

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 204 days.

(21) Appl. No.: 13/573,508

(22) Filed: Sep. 19, 2012

(65) Prior Publication Data

US 2014/0082805 P1 Mar. 20, 2014

(51) Int. Cl.
*A01H 5/00* (2006.01)

(52) U.S. Cl.
USPC ..... Plt./417

(58) Field of Classification Search
CPC ..... A01H 5/025; A01H 5/02; A01H 5/00
USPC ..... Plt./417
See application file for complete search history.

*Primary Examiner* — June Hwu
(74) *Attorney, Agent, or Firm* — Klarquist Sparkman, LLP

(57) ABSTRACT

A new and distinct *Coreopsis* plant named 'Desert Coral' characterized by large daisy-type flowers that grow to 3.5 cm in diameter, pink orange flowers with a dark red eye, grass green foliage on strong, upright, short stems, flowering for the whole summer, and a upright, mounding habit.

1 Drawing Sheet

Botanical denomination: *Coreopsis* hybrid.
Variety designation: 'Desert Coral'.

BACKGROUND OF THE INVENTION

The present invention relates to a new and distinct cultivar of *Coreopsis* and given the cultivar name 'Desert Coral'. *Coreopsis* is in the family Asteraceae. This new cultivar originated from an open pollinated cross using proprietary unprotected plants in the field. Seedlings were evaluated for new flower colors in large flowered, compact, free flowering habits. The new cultivar was selected for its new flower color.

Compared to *Coreopsis* 'Pumpkin Pie' (U.S. Plant Pat. No. 22,519), the new cultivar has flowers that are pink orange with a red eye rather than deep orange with a red eye. The new cultivar is taller.

SUMMARY OF THE INVENTION

The following traits have been repeatedly observed and are determined to be the unique characteristics of the new variety. These characteristics in combination distinguish *Coreopsis* 'Desert Coral' as a new and distinct cultivar:

1. large daisy-type flowers that grow to 3.5 cm in diameter,
2. pink orange flowers with a dark red eye,
3. grass green foliage on strong, upright, short stems,
4. flowering for the whole summer, and
5. an upright, mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

FIG. 1 shows a nine-month-old *Coreopsis* 'Desert Coral' growing in the one gallon container in August in Canby, Oreg. The plant was grown in full sun.

FIG. 2 shows a close up of the flowers of the same plant.

DETAILED PLANT DESCRIPTION

The following is a detailed description of the new *Coreopsis* cultivar based on observations of nine-month-old specimens growing in one gallon containers in full sun under typical outdoor conditions in early August in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on *The Royal Horticultural Society Colour Chart,* 5$^{th}$ edition.

Plant:

*Type*.—Herbaceous perennial.
*Hardiness*.—USDA Zones 7 to 9.
*Size*.—33 cm wide and 31 cm tall to top of inflorescences.
*Form*.—Upright mound.
*Vigor*.—Excellent.
*Roots*.—Fibrous, stems root easily from stem cuttings.

Stem:

*Type*.—Ascending.
*Size*.—To about 23 cm tall to where branches for flowering and 8 mm wide.
*Number of stems from the crown*.—About 4.
*Internode length*.—0.5 cm to 3 cm.
*Surface*.—Glabrous.

*Color*.—Green 137A except at base where Grey 200A.

Leaf:

*Type*.—Simple.

*Size*.—Grows to 5 cm long and 4 mm wide.

*Shape*.—Linear.

*Arrangement*.—Opposite.

*Margins*.—Entire.

*Apex*.—Acute.

*Venation*.—Pinnate.

*Surface texture*.—Glabrous on top and bottom sides.

*Petiole*.—None, sessile.

*Color*.—Topside Yellow Green 147A, bottom side Yellow Green 147B.

Inflorescence:

*Type*.—Long stalked terminal heads of daisy type inflorescences.

*Peduncle*.—5 cm to 8.5 cm long, 1 mm wide, glabrous, Green 137A.

*Size*.—Grows to 4 cm wide and 5 mm deep.

*Immature* (*closed bud*).—6 mm deep and 6 mm wide, ovoid, glabrous, top Greyed Orange N170A blending to Yellow Green 147A on bottom.

*Receptacle*.—Disc shaped, 3 mm wide and 1.5 mm deep, Yellow Green 146B.

*Phyllary*.—In two series; inner series broadly campanulate with 8 lobes, grows to 12 mm wide and 5 mm deep, each lobe ovate, margin entire, tip acute, glabrous on both sides, 7 mm long and 3 mm wide; top and bottom side Greyed Orange N170A on top end blending to Yellow Green 147A on base; outer series stellate, with 8 lobes, grows to 5 mm wide and 3 mm deep, each lobe ovate, margin entire, tip acute, glabrous on both sides, Green 137A on both sides.

*Lastingness*.—Each inflorescence lasts about a week on the plant.

Florets:

*Type*.—In composite heads.

*Ray florets*.—8 in number with no pistil or stamen, obovate with the tip three lobed with lobes obtuse and notched and the central lobe the longest and most notched, entire on both sides, grows to 20 mm long, 11 mm wide, glabrous, topside Greyed Orange N170A with basal eye Greyed Purple 187B; bottom side Greyed Orange 177C.

*Disc*.—Conic, deeper with maturity, 7 mm wide and becoming 3 mm deep with maturity; Greyed Purple 187A.

*Disc florets*.—With stamen and pistil, about 90 in number, 6 mm long and 1.5 mm wide, tubular; corolla 3 mm long, tube Yellow13B inside and out, 4 lobes Greyed Purple 187A on both sides; pistil 1, 6 mm long, ovary 1.5 mm long, White NN155D, style 4 mm long, extruding, with 2-branched stigma, stigma Orange 26A blending to style Orange 26C; stamen 5, anthers 2 mm long, Greyed Purple N186B, pollen Orange 26B.

*Bloom period*.—July through October in Canby, Oreg.

*Fragrance*.—Slight.

*Seed*.—None seen.

*Fertility*.—Infertile.

Disease and pests: No pests or diseases have been observed on plants grown under commercial conditions in Canby, Oreg. No resistances are known.

I claim:

1. A new and distinct *Coreopsis* plant as herein illustrated and described.

* * * * *

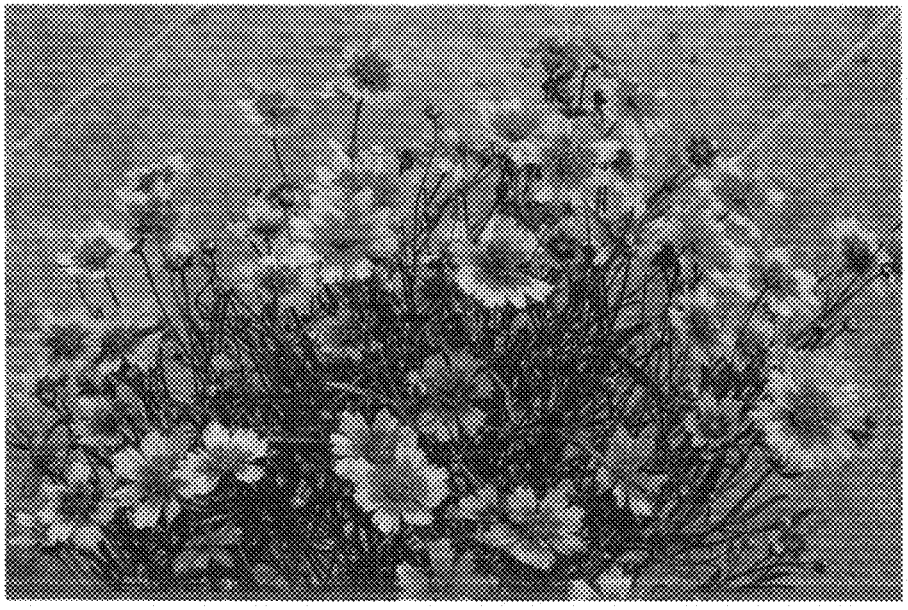

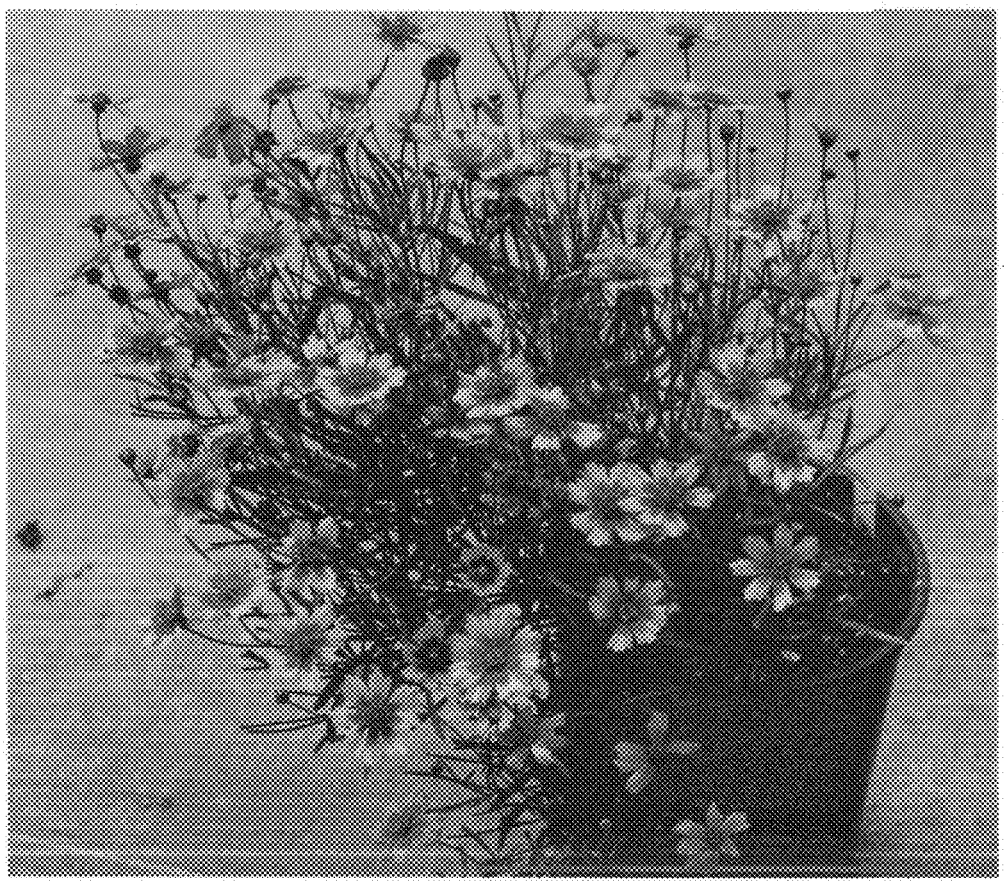
FIG. 1 above, FIG. 2 below